United States Patent [19]
Zweig

[11] Patent Number: 5,246,446
[45] Date of Patent: Sep. 21, 1993

[54] UTERINE INCISION COMPRESSION DEVICE

[76] Inventor: Jeffrey L. Zweig, 41356 Morada Ct., Fremont, Calif. 94539

[21] Appl. No.: 542,976

[22] Filed: Jun. 25, 1990

[51] Int. Cl.⁵ ............................................. A61B 17/42
[52] U.S. Cl. .................................... 606/119; 606/201; 604/356
[58] Field of Search ............... 606/112, 114, 115, 119, 606/201, 121, 122, 123, 151; 604/115, 356

[56] References Cited

U.S. PATENT DOCUMENTS 3,774,614  11/1973  Cook ................................... 606/201
4,633,865  1/1987  Hengstberger et al. ............ 606/201

*Primary Examiner*—Michael H. Thaler
*Attorney, Agent, or Firm*—Glen R. Grunewald

[57] ABSTRACT

A surgical instrument useful for performing Caesarean sections including a frame of stiff, springy material connected to a handle at either end of its long direction, the frame being dish-shaped with its convex side facing the handle, the frame being used by being pressed firmly against the uterus wall and an incision is made in the open center of the frame whereby uterine blood vessels are compressed and bleeding in the field of the operation is diminished.

9 Claims, 3 Drawing Sheets

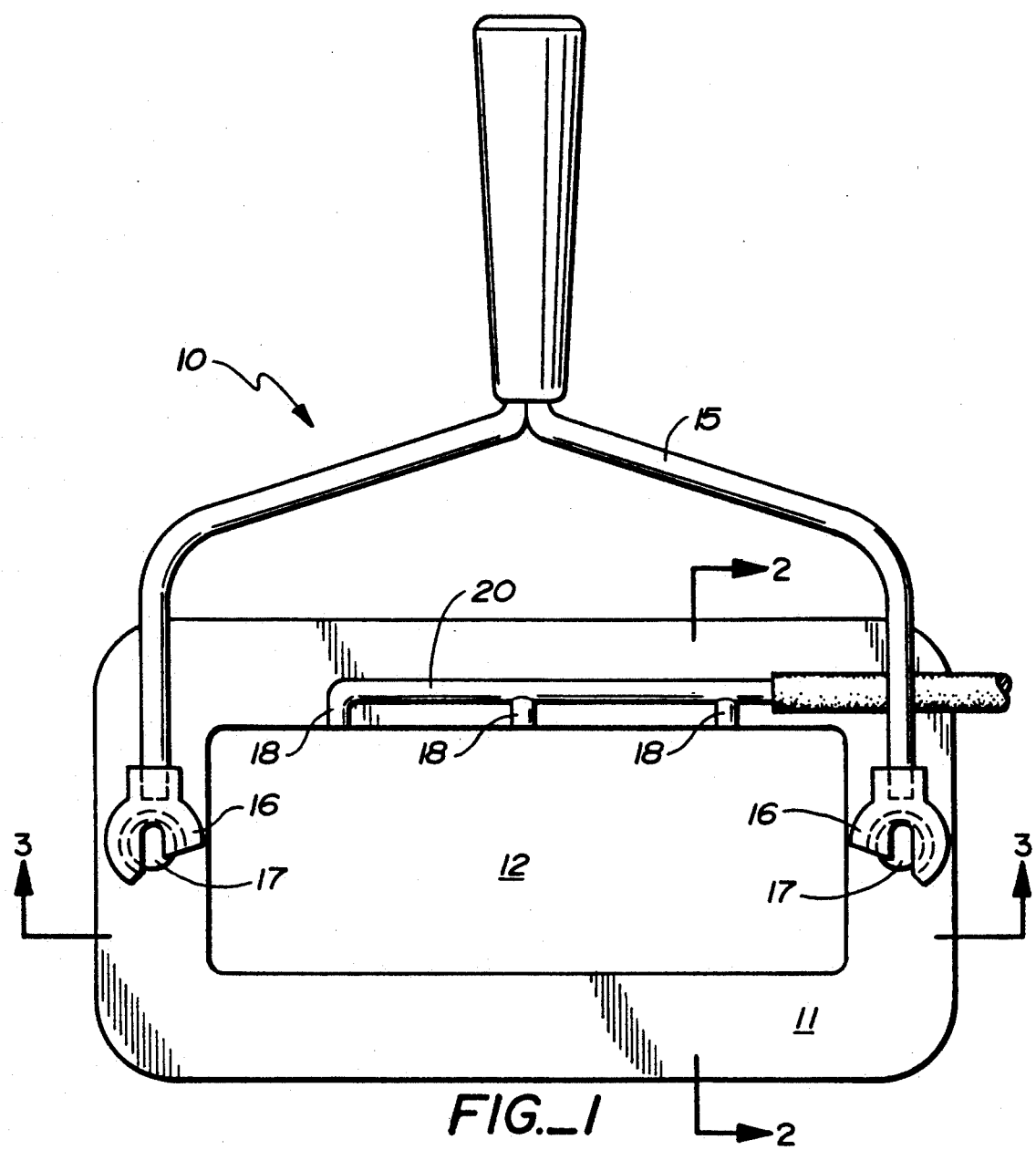
FIG._1
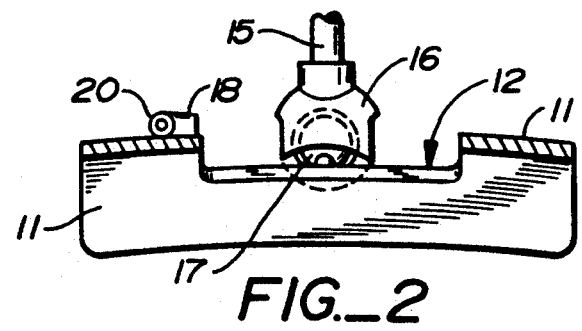
FIG._2

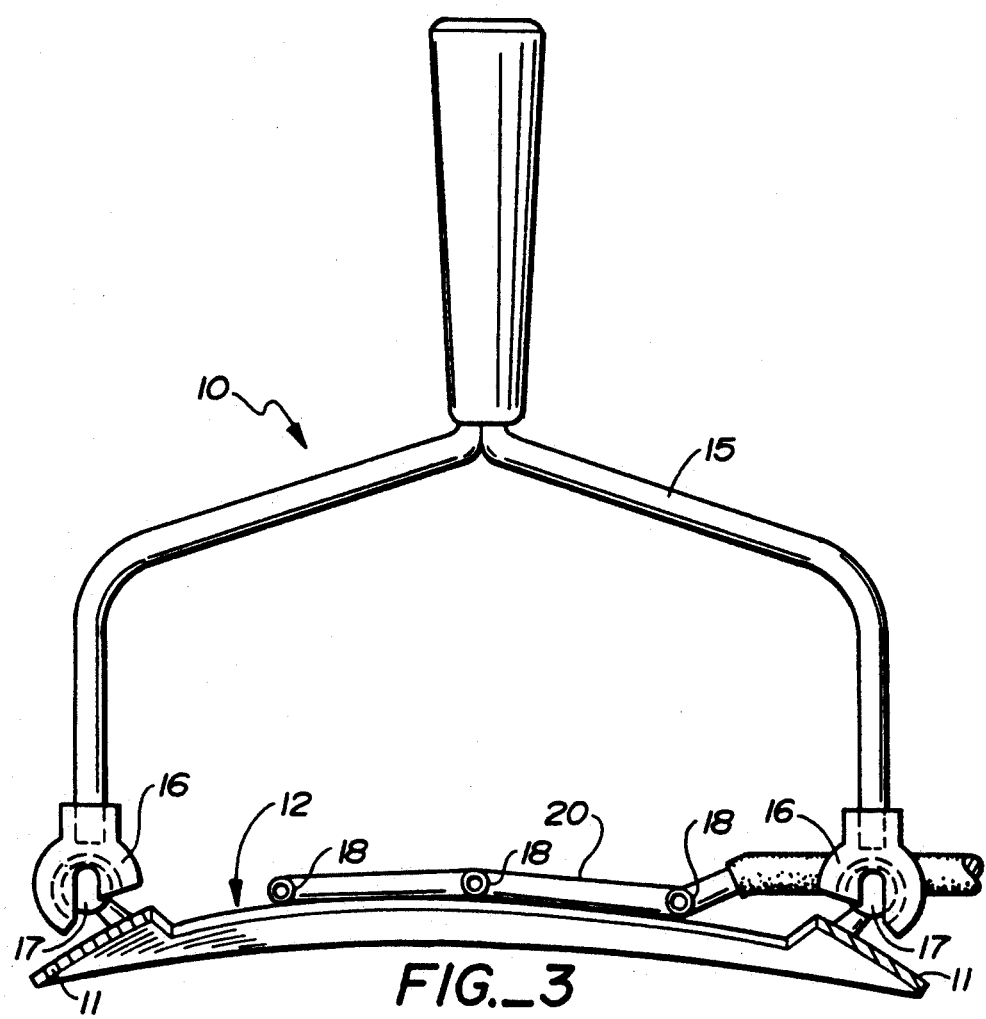
FIG._3
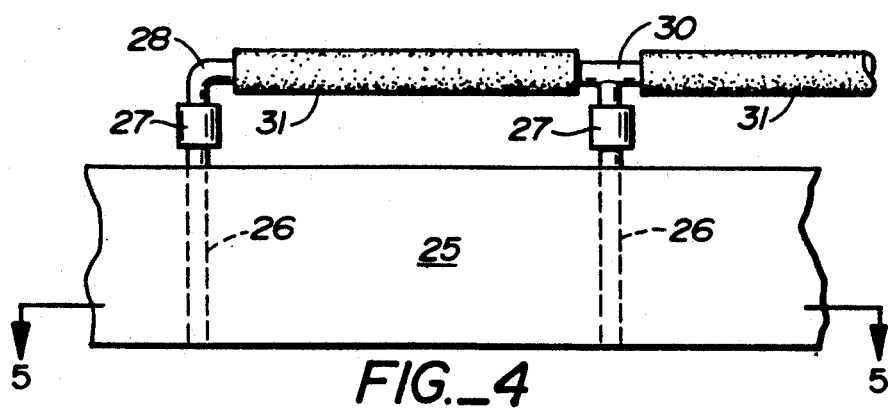
FIG._4
FIG._5

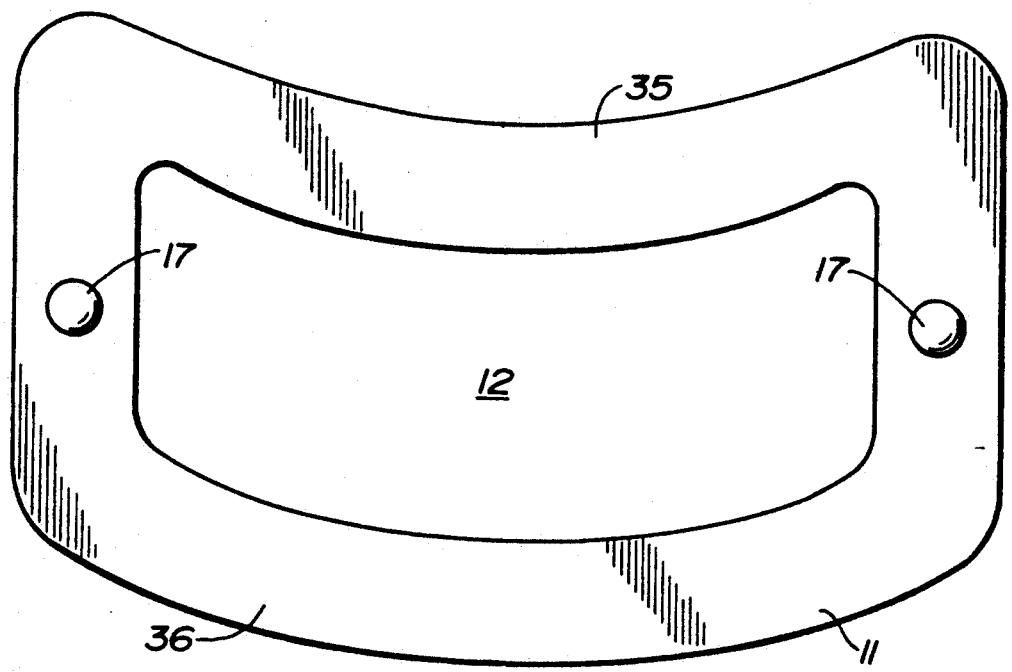
FIG._6

UTERINE INCISION COMPRESSION DEVICE

FIELD OF THE INVENTION

This invention is in the field of surgical devices, particularly devices useful in the performance of Caesarean sections.

BACKGROUND ART

Caesarean sections, hereinafter C-sections, are performed when vaginal birth is either not possible or is contraindicated by the condition of the mother or of the fetus. C-sections are performed by first incising the abdomen wall longitudinally from a point below the navel to a point above the symphysis. The incision is then retracted to expose the peritoneum which is then incised transversely to expose the uterus.

The uterus may be incised either transversely or longitudinally to gain access to the fetus which is removed from the uterus through the incision. It is preferred that the incision through the uterus be transverse and through the lower portion of the uterus wall because the upper portion is thicker and more vascular. Accordingly, a transverse incision through the lower portion of the uterus does not bleed as copiously and being thinner it heals better.

It is important to keep the surgical field free from blood. Loss of blood endangers the patient and bleeding obstructs the surgeon's field of vision. Controlling bleeding in a C-section is difficult because the uterus wall is very vascular.

DISCLOSURE OF THE INVENTION

This invention is a device that is useful in the performance of C-sections. The device provides a relatively unobstructed field of view for the surgeon and greatly diminishes bleeding from an incision in the uterus wall. In a preferred embodiment of the invention the device may be operated using only one hand whereby the surgeon's assistant has a free hand to perform other tasks and the region around the incision is not obstructed with instruments and operator's hands, leaving the field of the operation both visible and accessible.

The device of this invention is a frame of thin, stiff but flexible material having an open center surrounded by the frame. The frame has a long dimension and a short dimension, the long dimension preferably being approximately 13-15 centimeters and the short dimension preferably being approximately 7-8 centimeters. The central opening in the frame also has a long dimension and a short dimension, the long dimension preferably being approximately 10-11 centimeters and the short dimension preferably being approximately 4-5 centimeters. In another preferred embodiment the frame is provided with a handle attached to it through means comprising a pivot, preferably a universal joint so that the frame can be pressed against the uterus wall by exerting force on the handle and it can be swung around the pivot to expose any portion of the field of the operation within the opening in the frame.

In another preferred embodiment of the invention the frame is shaped to have a convex side and a concave side with the convex side facing the handle so that when it is in use the concave side can be pressed against the uterus wall. It is also preferred that the concave-convex shape be in both the long direction and the short direction of the frame so that it has a shallow dish shape. It is also preferred that the short edges of the frame be substantially straight lines while the long edges of the frame are curved in the same direction and to the same degree so that the frame can conform closely to the shape of a rounded uterus wall.

In another preferred embodiment the frame supports drain tubes opening in the central opening and being attachable at the other end to a suctioning device.

BRIEF DESCRIPTION OF THE DRAWINGS

FIG. 1 is a plan view of a device embodying this invention illustrating the handle of the device lying in a plane substantially parallel to the plane of the frame.

FIG. 2 is a cross-section of the device of FIG. 1 taken along the plane of the line 2—2.

FIG. 3 is a cross-section of the device illustrated in FIG. 1 taken along the plane of the line 3—3.

FIG. 4 is a partial-plan view of another device embodying this invention.

FIG. 5 is a cross-section of the device of FIG. 4 taken along the plane of the line 5—5.

FIG. 6 is a plan view of another device embodying the invention.

BEST MODE FOR CARRYING OUT THE INVENTION

The device illustrated in FIG. 1 is generally designated 10. It includes a plate-like frame 11 having a central opening 12. The frame is made of stiff but flexible sheet material. In the illustrated embodiment the frame is provided with a handle 15 that is connected to the frame with a universal joint formed of a ball segment 17 on the frame and a socket segment 16 on the handle. The frame must be stiff enough so that when it is pressed against a uterus wall with the handle it will compress the region of the uterus wall under the frame to provide a tourniquet effect to stem the flow of blood from an incision but it must be flexible enough so that it can conform to the shape of the uterus wall when it is forced against it. The frame 11 may be made of material such as thin stainless steel sheet or plastic.

As illustrated in FIG. 2, the frame is bowed or curved in its short dimension and as illustrated in FIG. 3 the frame is bowed or curved in its long dimension so that it has a shallow, dish-like configuration. The frame is bowed so that the convex side is provided with the universal joint segments.

In the embodiment of the invention illustrated in FIGS. 1, 2 and 3, a number of drain tubes 18 are positioned on the convex side of frame 11 so that they open into the central opening 12. The drain tubes are connected to a manifold 20 which in turn may be connected to suctioning means, not shown, so that any blood entering the opening in the frame may be suctioned away to keep the field of the operation visible. Manifold 20 is made of flexible tubing so as to not influence the flexibility of frame 11.

Another embodiment of the invention is illustrated in FIGS. 4 and 5. In the embodiment of FIGS. 4 and 5, the frame is formed of two sheets of material 11 and 25 and the drain tubes 26 are positioned between them. The thicknesses of the plates 11 and 25 ar adjusted to provide the device the right degree of stiffness and flexibility. The drain tubes 26 extend beyond the frame formed by the sheets 11 and 25 and are connected with couplings 27, appropriate elbows 28 and T's 30, and flexible tubing 31 to form a manifold that is connected to a suctioning device to draw blood away from the field of the operation. The construction shown in FIGS. 4 and 5 is advantageous because the openings of tubes 26 are virtually at the level of the surface of the uterus wall when the uterus is compressed by exerting force on the handle 15. The device of this invention does not require drain tubes. When the device does not include drain tubes blood may be removed from the operation site by hand.

FIG. 6 illustrates an embodiment of the invention wherein the device is not in the form of a regular geometric figure. The device of FIG. 6 has a top-frame element 35 and bottom-frame element 36 that are bowed in the same direction so that the frame 11 will come in contact with the uterus wall asymmetrically. The device of FIG. 6 is particularly desirable for preventing or diminishing bleeding when the lower part of the uterus is incised transversely because it conforms very well to the globular lower wall portion of the uterus of a pregnant woman. The device illustrated in FIG. 6 may also be dish-shaped.

When a longitudinal incision is to be made a device having the contours of the frame of FIG. 1 would be used. The slightly concave dish shape of the device of FIGS. 1, 2 and 3 is useful for both longitudinal and transverse incisions because that shape also conforms to the globular shape of the uterus of a pregnant woman. The device of this invention may have other shapes, such as oval.

The device is used in performing a C-section only after the uterine wall is exposed. The incision through the abdomen is made in the usual way and the bleeding from that incision is controlled by known methods. The abdominal incision is drawn apart by retractors and the lowermost portion of the uterus is exposed. The peritoneum is also incised and separated from the uterus wall. When the uterus wall is exposed the device of this invention is placed against it in the position where an incision through the uterus wall will be made within the opening of the frame and will run the long dimension of the opening. The frame is pressed against the uterus wall firmly enough to restrict the flow of blood through the blood vessels beneath the frame after which the surgeon incises the uterus wall in the usual manner to produce an opening therein sufficiently large to remove the fetus from the uterus. If a larger opening is needed the device may be moved so that any extension of the incision will be within the central opening of the frame. The force exerted against the uterus wall by the device of this invention eliminates most of the bleeding that such an incision will produce so that the surgeon has an unobstructed view of the area of the incision, the patient has minimum loss of blood, and the difficulties of seeing and manipulating the uterus and the fetus are greatly diminished. It is necessary to remove the device of this invention from contact with the uterus wall to remove the fetus from the uterus. When the fetus is removed from the uterus, the work of sewing the incision can be performed rapidly and in the usual manner to complete the performance of the C-section.

I claim:

1. A device to diminish bleeding in the performance of a Caesarean section comprising: a frame of stiff, springy material having a long axis and a short axis and an open mid-portion surrounded by said frame, means on said frame to connect a handle on opposite sides of said frame along said long axis.

2. The device of claim 1 wherein said means to connect a handle comprises a segment of a pivot.

3. The device of claim 2 wherein said pivot comprises a universal joint.

4. The device of claim 1 wherein said frame is arcuate in the long direction.

5. The device of claim 1 wherein said frame is arcuate in the long direction and said means to connect a handle are on the convex side of said frame.

6. The device of claim 1 wherein said frame is arcuate in the short direction.

7. The device of claim 1 including a drain tube connected to said frame and opening in said mid-portion.

8. The device of claim 1 wherein the short edges of said frame are substantially straight and substantially parallel and the long edges of said frame are curved in the same direction and to be substantially parallel.

9. A device to reduce bleeding during the performance of a Caesarean section comprising two, spaced frames of springy material connected together to superimpose one another and having a long axis and a short axis, each of said frames having an open mid-portion of the same size and shape as the other of said frames, one of said frames having means to connect to a handle on opposite sides of the open mid-portion thereof along said long axis, drain tubes positioned in the space between said frames and opening between the open mid-portions of said frames.

* * * * *